(12) United States Patent
Tabibiazar et al.

(10) Patent No.: US 7,495,024 B2
(45) Date of Patent: Feb. 24, 2009

(54) PHENYLALKYL N-HYDROXYUREAS FOR COMBATING ATHEROSCLEROTIC PLAQUE

(75) Inventors: Raymond Tabibiazar, Menlo Park, CA (US); Melisa Cooper, Princeton Jct, NJ (US); Thomas Quertermous, Stanford, CA (US); Adeoye Olukotun, Hopewell, NJ (US)

(73) Assignee: VIA Pharmaceuticals, Inc., San Francisco, CA (US)

( * ) Notice: Subject to any disclaimer, the term of this patent is extended or adjusted under 35 U.S.C. 154(b) by 51 days.

(21) Appl. No.: 11/499,924

(22) Filed: Aug. 7, 2006

(65) Prior Publication Data

US 2008/0033034 A1    Feb. 7, 2008

(51) Int. Cl.
*A61K 31/341* (2006.01)
*A61K 31/381* (2006.01)
*C07D 307/56* (2006.01)
*C07D 333/30* (2006.01)

(52) U.S. Cl. .................. 514/438; 514/461; 549/61; 549/474

(58) Field of Classification Search .......... 514/438, 514/461; 549/61, 474
See application file for complete search history.

(56) References Cited

U.S. PATENT DOCUMENTS

| 5,288,751 A * | 2/1994 | Brooks et al. ............... 514/438 |
| 2005/0113408 A1 | 5/2005 | Helgadottir |
| 2006/0019269 A1 | 1/2006 | Helgadottir |

OTHER PUBLICATIONS

The International Search Report and Written Opinion by the International Searching Authority, issued on May 27, 2008, in the PCT application No. PCT/US07/16030.

* cited by examiner

*Primary Examiner*—Rei-Tsang Shiao
*Assistant Examiner*—Janet L Coppins

(57) ABSTRACT

The method of treating patients be administering phenylalkyl N-hydroxurea derivatives for combating atherosclerotic plaque and cardiovascular diseases and compositions for this use.

20 Claims, 2 Drawing Sheets

EXTENT OF ATHEROSCLEROTIC DISEASE: 1- SLIGHT, 2- MODERATE, 3- HEAVY, 4- VERY HEAVY

ATHEROSCLEROSIS EXTENT OF DISEASE: 1- SLIGHT, 2- MODERATE, 3- HEAVY, 4- VERY HEAVY

HISTOPATHOLOGICAL EXTENT OF ATHEROSCLEROTIC LESIONS IN THE AORTIC ROOT OF apoE-DEFICIENT MICE. (A) AT MAXIMUM DOSE OF 50mg/kg, COMPOUND X RESULTS IN ~45% REDUCTION OF ATHEROSCLEROTIC PLAQUE FORMATION (p<0.001). (B, C) REPRESENTATIVE IMAGES OF AORTIC ROOT OF apoE-DEFICIENT MICE TREATED WITH VEHICLE VS. COMPOUND_50mg/kg, RESPECTIVELY.

PHENYLALKYL N-HYDROXYUREAS FOR COMBATING ATHEROSCLEROTIC PLAQUE

FIELD OF THE INVENTION

This invention is in the field of preventing and treating atherosclerotic plaque and cardiovascular diseases.

BACKGROUND OF THE INVENTION

The build up of fat-laden deposits on vessel walls as atherosclerotic plaque causes progressive narrowing in the vessel, such as in a carotid or coronary artery. Eventually, lumen or blood flow within the vessel is reduced to such a level that tissue, such as a heart muscle or brain tissue, is starved of oxygen-carrying blood which produces cardiovascular disease resulting in a heart attack, stroke or peripheral ischemia (reduced blood flow to feet or legs). In this process, low-density lipoproteins (LDLs) and immune system cells accumulate in the vessel wall and attract immune system cells into the vessel wall as well. Immune system cells ingest the modified LDLs, giving rise to fatty droplets, which constitute a lipid core of the plaque. The immune system cells secrete enzymes that degrade collagen of the fibrous cap of the plaque and prevent the development of new collagen fibers to repair the cap damage. The weakening of the cap may result in plaque rupture during which the blood of the lumen intermingles with the lipid core, rich in proteins that foster blood coagulation. As a result, a clot forms and the vessel may be occluded. This sudden occlusion of the blood vessel reduces or stops blood flow to the tissue, which results in death of heart muscle or brain tissue due to lack of oxygen-carrying blood resulting in heart attack or stroke. These acute events relating to plaque rupture are the major causes of morbidity and mortality in patients suffering from cardiovascular diseases.

Plaque composition in arteries is indicative of the risk of acute coronary syndromes. Soft plaque includes a high lipid concentration, a thin fibrous cap and inflammatory cells. Plaques with these characteristics are at increased risk for rupture and the associated acute events.

In the past, the build-up of atherosclerotic plaque has been treated by the use of anti-hypercholesterolemia and anti-hyperlipidemia agents to prevent the build-up of blood cholesterol. While these agents have been successful in reducing the levels of cholesterol and lipids in the blood, they do not directly treat the underlying causes of plaque rupture which lead to a risk of acute events. Therefore patients treated with existing agents may still be prone to plaque rupture and acute events. In some cases atherosclerotic plaque has been believed to have been caused by influenza viruses resulting in the recommendation of anti-viral drugs for treating atherosclerotic plaque. See Thumpey, Bassler, et al Science vol. 310 pg. 77 (Oct. 7, 2005). Additionally, bacterial infection due to Chlamydia pneumonia has previously been implicated in the development of atherosclerosis and coronary artery disease resulting in the recommendation of antibiotics such as gatifloxacin (*N Engl J Med.* 2005 Apr. 21; 352(16):1646-54) or azithromycin (Circulation 2000 Oct. 10; 102(15):1755-60) for the treatment of atherosclerotic plaque. However, these agents have not proven to be effective in preventing and reversing plaque build-up. Therefore, it is long to be desired to provide an agent which will be effective preventing and treating cardiovascular diseases caused by atherosclerotic plaque through stabilizing the plaque and as well as preventing the formation of atherosclerotic plaque thereby reducing the risk of plaque rupture and acute events.

SUMMARY OF INVENTION

Figure 1:
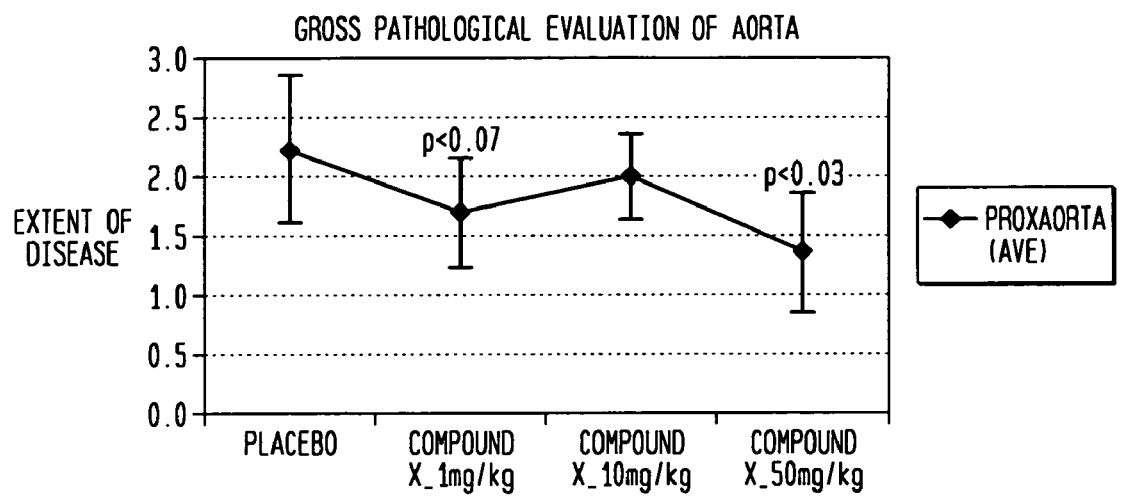
FIG. 1 is a graph setting forth the results for the pathological evaluation and dose response of the aortas of 12-week old ApoE-deficient mice who were treated for a further 28 days in accordance with this invention and with a vehicle placebo.

In accordance with this invention, it has been found that the administration to patients of compounds of the formula:

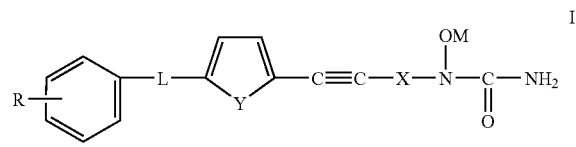

wherein R is hydrogen, lower alkyl, halogen, trifluoromethyl, lower alkoxy or hydroxy; Y is —O— or —S—; L is lower alkylene and lower alkenylene; and X is a branched or straight chain lower alkylene and M hydrogen, a pharmaceutically acceptable cation or a pharmaceutically acceptable metabolically cleavable group;

or pharmaceutically acceptable salts thereof, are effective in combating by preventing or treating atherosclerotic plaque through stabilizing and/or reversing the build-up of atherosclerotic plaque as well as through preventing the formation of atherosclerotic plaque. In this manner the compounds of Formula I and their salts are effective in treating and preventing atherosclerotic plaque which is one of the causes of cardiovascular diseases.

In addition it has been found that the compounds of Formula I and their pharmaceutically acceptable salts are effective in treating the other symptoms of cardiovascular diseases such as shortness of breath and chest pains. This effect makes the compounds of Formula I and their salts effective in combating cardiovascular diseases in general.

The N-hydroxyurea compounds of formula I are disclosed in Brooks et al., U.S. Pat. No. 5,288,751, Feb. 22, 1994, as inhibitors of 5-lipoxygenase activity and leukotriene biosynthesis which inhibitors have found useful in the treatment of allergic and inflammatory disease states. In fact certain N-hydroxyurea compounds have been used to treat asthma. In particular the N-hydroxyurea compound such as zileuton, have been found to be useful in treating asthma. However, unlike these N-hydroxyurea compounds used for treating asthma such as zileuton, the N-hydroxyureas of formula I, when used for combating plaque do not have high toxicity.

DETAILED DESCRIPTION

In accordance with this invention, it has been discovered that the administration to patients of compounds of formula I, their pharmaceutically acceptable salts, or their pharmaceutically acceptable hydrolyzable esters are effective in treating patients susceptible to heart attack, stroke or peripheral arterial disease caused by atherosclerotic plaque through combating atherosclerotic plaque formation. The particularly preferred compound of formula I for treating said patients in this manner is the compound: N-[3-[5-[(4-fluorophenyl)methyl]-2-thienyl]-1-methyl-2-propynyl]-N-hydroxyurea which has the formula:

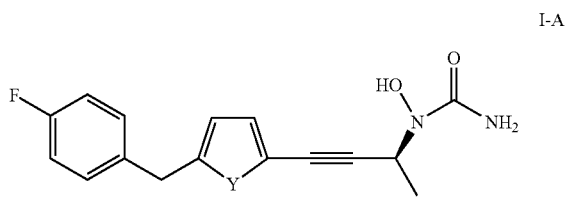

The most preferred embodiment of the compound of formula I-A is the isomeric compound of formula I-A having the 1-R configuration.

As stated hereinabove, the compounds of formula I or their pharmaceutically acceptable salts combat cardiovascular disease, such as heart attacks and strokes, caused by the buildup or formation atherosclerotic plaque by preventing the formation of atherosclerotic plaque or by stabilizing the atherosclerotic plaque in patients who have been diagnosed with such plaque and decreasing the risk of plaque rupture and acute events. In such a manner, the compounds of formula I or their pharmaceutically acceptable salts act as a prophylaxis against or as a treatment for cardiovascular disease such as heart attacks and strokes caused by the buildup or formation atherosclerotic plaque.

In addition the administration of the compounds of formula I or their pharmaceutically acceptable salts to patients not only combats atherosclerotic plaque but reduces and/or stabilizes the other causes and symptoms of cardiovascular diseases. This effect is shown by the reduction of these causes and symptoms as shown by the standard markers used to diagnose and monitor cardiovascular disease. Therefore the compounds of formula 1 and their pharmaceutically acceptable salts can be used in treating or preventing cardiovascular diseases. Cardiovascular diseases include cardiac or arterial diseases as well as peripheral vascular diseases, which if untreated, could result in a heart attack, stroke or damage to limbs or other organs (e.g., kidneys).

The term "patient" includes any human or mammal subject who is susceptible to cardiovascular disease. These include patients who have been diagnosed as having atherosclerotic plaque, patients who have already had heart attacks and/or strokes and/or other manifestations of peripheral arterial disease or patients who are otherwise susceptible to cardiovascular diseases such as heart attacks or strokes in view of their family history, genetic testing or the presence of other risk factors (e.g., smoking, hypertension, high cholesterol, diabetes, obesity). Where the compound of formula I or its pharmaceutically acceptable salts is used for combating heart attacks in patients who are otherwise susceptible to heart attacks or strokes, which have not been diagnosed as having atherosclerotic plaque but rather had a history of cardiovascular disease, such as heart attacks or strokes or have a susceptibility to such cardiac diseases heart attacks or strokes as determined through such means as genetic testing, family history or the presence of additional risk factors, the compound of formula I is used as a prophylaxis for prevention of such cardiovascular diseases such as heart attacks and strokes in these patients. On the other hand, where the patient has been diagnosed as having atherosclerotic plaque, then the administration of the compounds of formula I or their pharmaceutically acceptable salts treat such atherosclerotic plaque to prevent further build-up, stabilize and/or to reduce the atherosclerotic plaque in the patient and decrease the risk of plaque rupture and acute events. In accordance with the preferred embodiment of this invention the patient is a human patient.

In accordance with this invention, it is discovered that when compounds of formula I or their salts are administered to patients, the compounds of formula I or their pharmaceutically acceptable salts exhibit their effect and minimize or eliminate the toxicity or adverse effects commonly associated with certain N-hydroxyureas. This allows the compounds of formula I or their pharmaceutically acceptable salts to be administered to human patients even at high dosages without producing the toxicity or degree of toxicity and concomitant level of adverse effects associated with certain N-hydroxyureas.

The patients can be diagnosed for the presence and/or the amount of atherosclerotic plaque by many conventional means, particularly by using various imaging systems used for this purpose. One of the most common methods for detecting or diagnosing atherosclerotic plaque is through angiography. Another means for detecting components of atherosclerotic plaque within human arteries is using computed tomography, electrocardiography, ultrasonography, nuclear imaging, stress testing and physical examination.

With respect to preventing cardiovascular diseases as well atherosclerotic plaque formation, the measurement of serum biomarkers provides an additional means for identifying patients at risk for cardiovascular diseases as well as for atherosclerotic plaque. Also a number of genes have been identified that are linked through mechanistic studies to cardiovascular diseases caused through the formation of atherosclerotic plaque. See Glass and Witztum (2001), *Cell*, 104: 503-16; Breslow (1996), *Science*, 272:685-88; Lussis (2000), *Nature*, 407:233-41. Genes with a known association with atherosclerotic plaque can be utilized to predict the susceptibility of patients, human and animal, to the risk of atherosclerotic plaque formation. Please note Wuttge et al. (2001), *Mol. Med.*, 7:383-92; Archachi et al. (2003), *Physiol. Genomics*, 15:65-74; Faber et al. (2002), *Curr. Opin. Lipidol.*, 13:545-552; McCaffrey et al. (2000), *J. Clin. Invest.*, 105:653-662 and Seo et al. (2004), *Arterioscler. Thromb. Vasc. Biol.*, 24:1922-7. Using microarrays of disease related gene expression, the impact of individual risk factors and perturbations on the expression of individual genes during disease development can be studied systematically without apriori knowledge of gene identity. The temporal expression patterns of genes can then be correlated with the well-described disease stages of the progression of atherosclerotic plaque and the risk of plaque rupture.

The patients are treated with the compounds of formula I or their pharmaceutically acceptable salts by administering the compound to the patient in an effective amount sufficient to treat or prevent the cardiovascular diseases caused by atherosclerotic plaque and can be patients who are diagnosed as having atherosclerotic plaque or patients who have had a previous history of cardiovascular disease or patients who have a family history of cardiac disease linked to atherosclerotic plaque or the presence of additional risk factors for atherosclerotic plaque or patients who, through genetic testing, have genes that are linked to cardiovascular diseases caused by the formation of atherosclerotic plaque. The patients so treated can be monitored before, during and after the treatment with respect to the atherosclerotic plaque as well as the other symptoms of cardiovascular disease. As set forth above, angiography is the most common method for detecting or diagnosing atherosclerotic plaque in patients being treated with the compounds of formula I or their pharmaceutically acceptable salts. Various means exist for diagnosing and determining the progress of the treatment of cardiovascular patients being administered the compounds of Formula I or their pharmaceutically acceptable salts is by monitoring the other symptoms of cardiovascular disease The means for monitoring these other symptoms of cardiovascular disease such as vascular inflammation is by use of the following biomarkers:

Ex-vivo leukotriene B4 (LTB4) synthesis in whole blood
Leukotriene E4 (LTE4) in urine
High sensitivity C-reactive protein (hsCRP)
Myeloperoxidase (MPO)
Monocyte chemotactic protein (MCP1)
M-CSF (CSF-1)
MIP-2 (Cxcl2)
Osteopontin (Spp1)
Peripheral blood RNA expression
DNA genotype The treatment can be followed by the physician by means of determining the efficacy of the compounds of formula I or their pharmaceutically acceptable salts in treating the patient either by determining the presence and/or amount of atherosclerotic plaque and /or determining the retarding of the disease by means of assessing these biomarkers before, after and during the treatment with the compounds of formula I or their salts. The treatment can be carried out by the physicians in accordance with the patient's requirements as determined by the presence and/or amount of atherosclerotic plaque in the patient during the treatment and or by means of these diagnostic tools.

The term "alkyl" refers to monovalent hydrocarbon group derived from a straight or branched chain saturated hydrocarbon by the removal of a single hydrogen atom. Lower alkyl groups contain from 1 to 6 carbon atoms and are exemplified by methyl, ethyl, n-iso-propyl, n-sec-iso-tert-butyl and the like.

The term "lower alkylene" denotes a divalent group derived from a straight or branched chain saturated hydrocarbon by the removal of two hydrogen atoms which lower alkylene group contains from 1 to 6 carbon atoms. Lower alkylene groups include methylene, 1,2-ethylene, 1,1-ethylene, 1,3-propylene, 2,2-dimethylpropylene and the like.

The term "lower alkenylene" denotes a divalent group derived from a straight or branched chain hydrocarbon containing at least 1 carbon-carbon double bond with the remainder of the carbon to carbon bonds being saturated and containing from 2 to 6 carbon atoms.

The term "lower alkoxy" denotes an alkoxy group where a lower alkyl is defined above attached to a molecular moiety through an oxygen atom. Representative lower alkoxy groups include methoxy, ethoxy, propoxy, butoxy and the like.

The term "halogen" includes all halogens, particularly, bromine, chlorine, fluorine and iodine.

The term "metabolically cleavable group" denotes a group which is cleaved in vivo to yield the parent molecule of the structural formulae indicated above wherein M is hydrogen. Examples of metabolically cleavable groups-include —COR, —COOR, —CONRR and —CH$_2$OR radicals where R is selected independently at each occurrence from alkyl, trialkylsilyl, carbocyclic aryl or carbocyclic aryl substituted with one or more of C$_1$-C$_4$ alkyl, halogen, hydroxy or C$_1$-C$_4$ alkoxy. Specific examples of representative metabolically cleavable groups include acetyl, methoxycarbonyl, benzoyl, methoxymethyl and trimethylsilyl groups.

By "pharmaceutically acceptable salt" it is meant those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 1977, 66:1-19. The salts can be prepared in situ during the final isolation and purification of the compounds of the invention, or separately by reacting the free base function with a suitable organic acid. Representative acid addition salts include acetate, adipate, alginate, ascorbate, aspartate, benzenesulfonate, benzoate, bisulfate, borate, butyrate, camphorate, camphersulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The compounds of formula I or their pharmaceutically acceptable salts which are used in accordance with the present invention may exhibit stereoisomerism by virtue of the presence of one or more asymmetric or chiral centers in the compounds. The present invention contemplates the various stereoisomers and mixtures thereof. Desired enantiomers are obtained by chiral synthesis from commercially available chiral starting materials by methods well known in the art, or may be obtained from mixtures of the enantiomers by resolution using known techniques.

In preventing and treating cardiovascular disease in patients by administering the compounds of formula I and their pharmaceutically acceptable salts as well as to stabilize and/or reverse the build-up of atherosclerotic plaque as well as retard the formation of atherosclerotic plaque, the compounds of formula I and their pharmaceutically acceptable salts can be administered systemically either by injection or orally. In general the compounds of formula I and their pharmaceutically acceptable salts can be administered to a human patient in any amount which is effective in preventing and treating cardiovascular disease in such patients and which will stabilize and/or reverse the build-up of atherosclerotic plaque as well as retard the formation of atherosclerotic plaque in such patient. In carrying out such treatment and prevention, the compounds of formula I and their pharmaceutically acceptable salts are preferably administered orally at a dosage of from about 0.2 to about 3.0 mg/kg of body weight of the patient per day. The dosages can be administered orally in solid oral unit dosage forms such as capsules, tablets, dragees, pills, powders, granules and the like, as well as liquid oral dosage forms such as solutions, syrups, suspensions, elixirs and the like. In general, the unit dosage form should contain the compounds of formula I or their pharmaceutically acceptable salts in amounts of from about 25 to 200 mg. Of the unit oral dosage forms, capsules and tablets are especially preferred. When the drug is administered orally, it is generally administered at regular intervals conveniently at meal times or once or twice daily.

When the compounds of formula I and/or their pharmaceutically acceptable salts are administered for treating patients which have not been diagnosed as having cardiovascular disease or as having atherosclerotic plaque, but have been diagnosed as being susceptible to cardiovascular disease, either through family history or the presence of other risk factors or through having previous heart attacks or strokes, the compounds of formula I and their pharmaceutically acceptable salts are effective in preventing cardiovascular disease or preventing the formation of atherosclerotic plaque. In administering the compounds of formula I and their pharmaceutically acceptable salts as a prophylactic, the same oral dosage forms that can be utilized for treating cardiovascular diseases are used.

The compounds of formula I above and their pharmaceutically acceptable salts are orally administered in the same manner as that described for the use of the compounds of formula I and their pharmaceutically acceptable salts for treating diagnosed cardiovascular disease.

The compounds of formula I and/or their pharmaceutically acceptable salts can be parenterally administered. The term "parenteral administration" refers to modes of administration which include intravenous, intramuscular, intraperitoneal, subcutaneous and intra articular injection and infusion. Pharmaceutical compositions for parenteral administration comprise pharmaceutically acceptable sterile aqueous or non-aqueous solutions, dispersions, suspensions or emulsions, as well as sterile powders for reconstitution into sterile injectable solutions or dispersions just prior to use. Examples of suitable aqueous and non aqueous carriers, diluents, solvents or vehicles includes water, ethanol, polyols such as glycerol, propylene glycol, polyethylene glycol and the like and suitable mixtures thereof, vegetable oils, such as olive oil, and injectable organic esters such as ethyol oleate.

The parenteral administration the compounds of formula I and their pharmaceutically acceptable salts can be administered at the same daily dosage as that for oral administration, generally from about 0.2 to about 3.0 mg/kg per day of the compounds of formula I or their pharmaceutically acceptable salts for treating or preventing cardiovascular disease such as a stroke or a heart attack.

The dosage, in the case for systemic administration, varies in accordance with the requirement of the individual patient as determined by the treating physician. In general, however, a daily systemic dose of about from 0.2 to about 3.0 mg/kg of body weight of the patient is preferred. The dosage can be administered as a single dosage or in several divided dosages proportionate with the dosage plan as determined by a physician in accordance with the requirements of the patient. In preparing the compositions for such systemic administration these compositions contain the compounds of formula I or their pharmaceutically acceptable salts and a pharmaceutically acceptable carrier compatible with said compound or its salt. In preparing such compositions, any conventional pharmaceutically acceptable carrier can be utilized.

As pointed out, solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, and tragacanth, and mixtures thereof.

EXAMPLES

In Examples 1 and 2 knockout mice deficient in producing the protein Apolipoprotein E [apoE] were used. ApoE-deficient mice are known to spontaneously develop atherosclerotic plaque at 12-16 weeks, which process is accelerated by feeding the mice a high fat diet. Because the atherosclerotic lesions found in these mice are histologically similar to those found in humans, the ApoE-deficient mice are used as a model for assessing the effects of a drug on atherosclerotic plaque in humans.

In the Examples compound X designates the compound: N-[3-[5-[(4-fluorophenyl)methyl]-2-thienyl]-1-methyl-2-propynyl]-N-hydroxyurea.

Example 1

This example was carried out on ApoE-deficient knockout mice who were before their normal development of atherosclerotic plaque which occurs in about 12 weeks to determine the effect of compound X i.e. the compound: (N-[3-[5-[(4-fluorophenyl)methyl]-2-thienyl]-1-methyl-2-propynyl]-N-hydroxyurea) on the prevention of plaque formation.

Four week old female ApoE knockout mice were fed a high fat diet (21% anhydrous milk fat and 0.15% cholesterol) for a period of eight weeks. The 12-week old ApoE-deficient mice were then randomized to receive vehicle (0.9% sterile saline administered at 5 mL/kg) or compound X and administered at three different doses: 1, 10 or 50 mg/kg, each in a volume of 5 mL/kg (from concentrations of 0.2, 2, 10 mg/mL, respectively)) daily for 28 consecutive days. Saline vehicle and doses of compound X were all prepared fresh daily and administered orally with a 22G gavage syringe. Doses were adjusted based on most recently obtained body weights.

There were two treatment groups and were treated as follows:

Treatment Group I 16 female mice/set for each dosage of compound X and for the saline vehicle, the dosages for the three sets of 16 mice were as follows: compound X at a dosage of 1 mg/kg, compound X at a dosage of 10 mg/kg and no compound X in the vehicle; and Treatment Group 2

16 female mice/set for each dosage of compound X and for the saline vehicle, the dosages for each set of 16 mice were as follows: compound X at 1 mg/kg, compound X at 50 mg/kg and no compound X in the vehicle.

Blood samples were collected from all mice by retrorbital bleed on Day 14 of dosing and at terminal sacrifice (28 days after initial dose). At terminal sacrifice, the thorax and abdomen were opened to allow cannulation of the heart through the left ventricle. The heart was perfused with 0.9% normal saline and animals were exsanguinated through a cut made in the posterior vena cava. After perfusion, the heart was isolated from the aorta at the heart/aorta junction, the aorta was isolated from the heart to the iliac juncture and the fat was removed. The heart and the aorta were then placed in saline on ice, and cleaned under a dissecting microscope until free of fat and connective tissues.

The gross qualitative atherosclerotic lesion analysis was performed on the aortas obtained from all mice given in FIG. 1 and the results of all examinations of the aortas were performed by operators blinded to the treatment arm. For qualitative assessment of the atherosclerotic process, given in Table 1, a standardized scoring system based on the extent and quality of the atherosclerotic plaque present in the aorta was used. Lesions were graded on a scale of 1 to 4: 1—slight, 2—moderate, 3—heavy and 4—very heavy as seen from the table given below.

TABLE 1

Scheme for Qualitative Assessment of the Extent and Quality of the Atherosclerotic Plaque

| Qualitative Assessment Score | Amount of plaque present | Proximal Aorta | Aortic Arch (AR) | Length of Aorta (AO) |
| --- | --- | --- | --- | --- |
| 1 | Slight (S) | ¼ of vessel circumferences filled with plaques | Plaques on approximately ⅓ of arch | Small sporadic plaques |
| 2 | Moderate (M) | ½ of vessel circumferences filled with plaques | Plaques on approximately ⅔ of arch | Plaques are more frequent and adjoining but still translucent |
| 3 | Heavy (H) | ¾ of vessel circumferences filled with plaques | Plaques on approximately all of arch | Plaques are opaque, hard to the touch and take up entire vessel space |
| 4 | Very Heavy (VH) | All filled with plaque | All filled with plaque | All filled with plaque |

The results which are given in FIG. 1 were analyzed by one-way analysis of variance (ANOVA) and Student's unpaired t-test comparing each treatment arm to the appropriate control arm.

As seen from FIG. 1, the results from this mouse model of atherosclerotic demonstrate that once daily administration of compound X at doses of 1, 10 and 50 mg/kg/day resulted in reductions in the extent of plaque in the proximal aorta of ApoE-deficient mice used to prepare the results in FIG. 1. As seen from FIG. 1 at the maximal dose of compound X (50 mg/kg/day), a significant reduction of plaque formation was observed in the proximal aorta (approximately a 40% reduction, $p<0.03$) compared to vehicle. The generally dose-dependent reduction in the extent of plaque formation on gross pathological evaluation in the proximal aorta is consistent, therefore, with related reduction in both plaque formation and disease progression in the early stages of disease. These results in FIG. 1 demonstrate that compound X is effective in preventing the build-up of atherosclerotic plaque.

Example 2

This example demonstrates the effect of compound X in ApoE-deficient knockout mice where atherosclerotic plaque had developed before compound X was used to treat the mice.

Four week old female ApoE-deficient knockout mice were fed a high-fat diet set forth in Example 1 for a period of 24 weeks to allow atherosclerotic plaque to build-up. The 28 week old ApoE-deficient mice were then randomized to receive vehicle (0.9% sterile saline administered at 5 mL/kg or compound X administered at two different doses, 10 mg/kg and 50 mg/kg, each in a volume of 5 mL/kg (from concentrations of 0.2 and 10 mg/L respectively) daily for 28 consecutive days. Saline vehicle and compound X were all prepared fresh daily and administered orally with a 22G gavage syringe. Doses were adjusted based on most recently obtained body weight. The following two treatment groups were tested and compared: 1) the first treatment group consisted of 20 female mice treated only with saline and 20 female mice treated with 10 mg/kg of compound X and 2) the second treatment group consisted of 20 female mice treated with vehicle and 20 female mice treated with 50 mg/kg of compound X.

The entire treatment was carried out by administering the vehicle or the dosage to the mice once a day for 28 days. During this treatment blood samples were collected by retrorbital bleed on day 14 of dosing and at the day of the terminal sacrifice which was 28 days after the initiation of dosing. At terminal sacrifice, aortas were harvested from 16 mice in each of the treatment groups and grossly evaluated, selected tissue from the remaining 4 mice per group were evaluated grossly and fixed and processed for histopathological analysis and quantitative determination of plaque burden. The results are given in FIG. 2 and FIG. 3.

Figure 2:
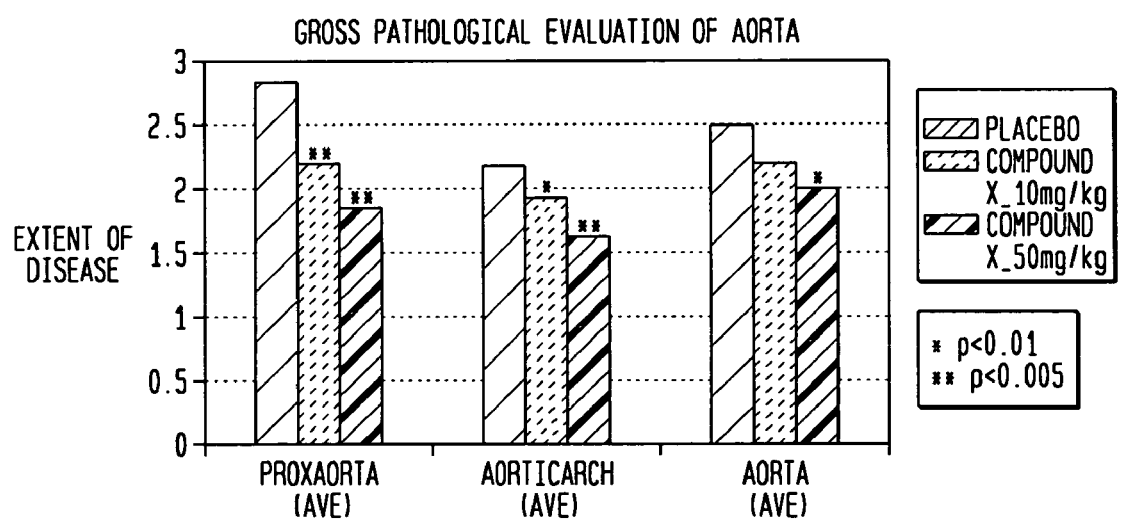
FIG. 2 is a graph of the pathological evaluation and dose response of the aortas of 28-week old ApoE-deficient mice that were treated for an additional 28 days in accordance with this invention and with a placebo.
Figure 3:
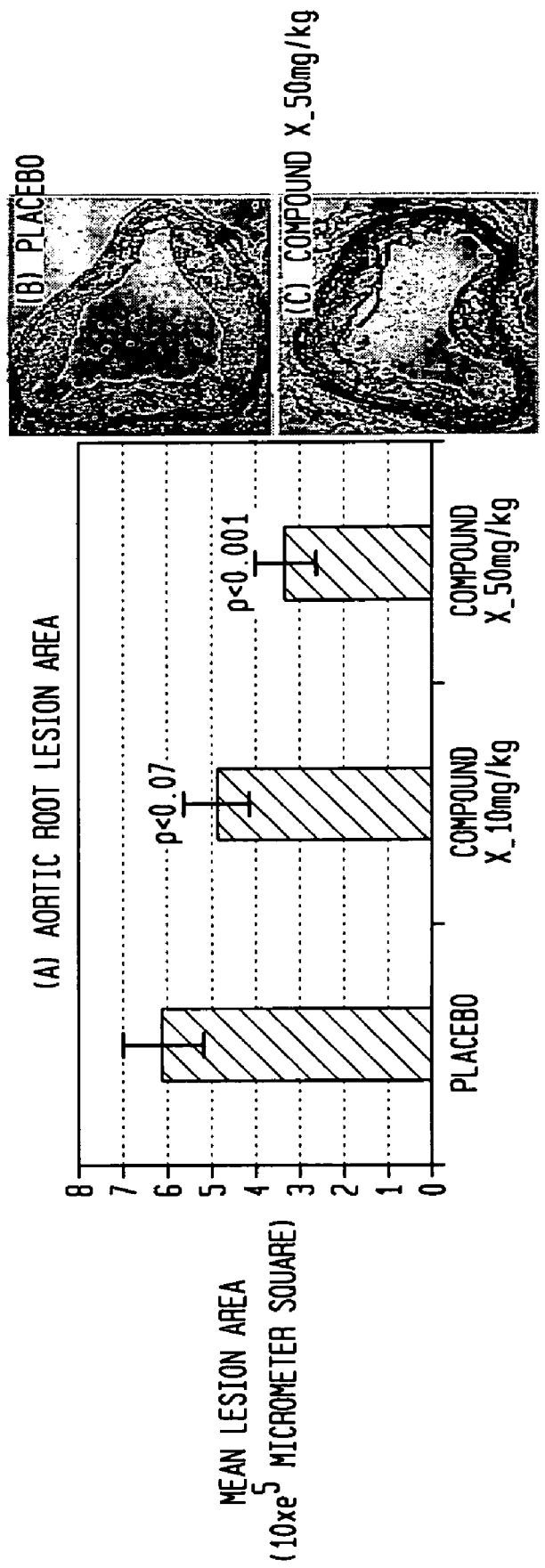
FIG. 3 is a graph of the histopathological extent of atherosclerotic lesions in the aorta root of 28-week old ApoE-deficient mice that were treated for an additional 28 days in accordance with this invention and with a vehicle.

For quantitative assessment of the atherosclerotic process, in FIG. 2 and FIG. 3, the aortic tree of mice was prepared and described by Tabibiazar, Wagner, et al. Physiol Genomics 22(2): 213-226 (2005). The amount of plaque/lesion area in the aortic root, as well as the entire aorta, was measured. Percent lesion areas were calculated as a total lesion area divided by the total surface area.

To obtain the results given in FIG. 2 and FIG. 3, the aorta and the heart samples obtained from 4 mice for each treatment protocol were profused with paraformaldehyde and transferred for histopathologoical analysis. All analyses were performed in a blinded manner. The upper-half of the heart was dissected, fixed overnight in formal-sucrose and paraffin embedded. Sequentially 7-μm thick sections were cut from the apex towards the base of the heart until the aortic valve leaflets appeared. From this point, 17 sections representing every second serial section over a distance of 238 μm were collected and stained with hematoxylin and eosin. The results achieved by the carrying out of the above procedure, in FIG. 2 and FIG. 3, with regard to this mouse model of atherosclerotic disease demonstrated that the daily oral administration of compound X both at 10 and 50 mg/kg/day led to statistically significant reductions in plaque burden in the proximal aorta and aortic arch when compared to the vehicle. FIG. 2 provides the results of the gross pathological evaluation of the aorta. It shows the results of plaque disease at the aorta, the aortic arch and the proximal aorta. The numbers 0-3 are as given in Table 1. As shown in FIG. 2, there was substantial reduction of atherosclerotic lesions in the proximal aorta, aortic arch, as well as the thoracic and abdominal aorta of the mice where the mice were treated with compound X either at 10 mg/kg/day or 50 mg/kg/day as compared with the vehicle. Most significant reduction is noted mainly in the proximal arch of the aortas in mice receiving the 50 mg/kg/dose of compound X.

For the quantitative assessment of the atherosclerotic process in FIG. 3, the amount of plaque/lesion area in the aortic root as well as the entire aorta was measured. Percent lesion area was calculated at total lesion area divided by total surface area.

The histopathological evaluation of the aortic root in ApoE-deficient mice demonstrated a dose dependent reduction of atherosclerotic plaque formation at both 10 mg/kg doses ($p<0.07$) and 50 mg/kg doses ($p<0.001$) of compound X as compared to vehicle animals. As seen from FIG. 2, the statistically significant reduction in mean lesion area of mice administered compound X at 50 mg/kg compared to the vehicle was approximately 45%.

The extent of plaque formation in the aorta was compared quantitatively in ApoE-deficient mice receiving vehicles to mice administered compound X at dosages of 10 and 50 mg/kg/day. FIG. 3 illustrates that the percent plaque area in the aortas of mice receiving compound X were substantially less compared to the aortas from mice administered the vehicle. The percent plaque lesion area in the vehicle mice was greater in the second experimental group compared to the first experimental group. FIG. 3 demonstrates that the comparison between the vehicle and the mice treated with compound X in each experimental group revealed marked reduction of percent plaque lesion area and this response was dose dependent.

The results suggest that orally administered compound X is associated with reduced atherosclerotic plaque by retarding the plaque progression and/or causing regression of the plaque.

Example 3

This example demonstrates the efficacy of treatment with Compound X in reducing atherosclerotic plaque and cardiovascular disease in patients. In this study the plaque levels were determined by use of Multidetector (64 slice coronary) Computerized Tomography (MDCT) scan indicative of such plaque in male and female patients suffering from Acute Coronary Syndrome (ACS). The efficacy of this treatment in reducing the effects of cardiovascular disease was determined by the use of biomarkers for this disease. For this randomized, double blind, placebo-controlled study, four groups each containing 50 clinically stable patients between the age of 30 and 80 years suffering an ACS event in the preceding twenty-one days (+/−3 days) are treated by oral administration of Compound X.

This treatment study is carried out by Compound X being orally administered to three treatment groups, the first treatment group being at a dose of 25 mg per day. To the second treatment Group, Compound X is orally administered at a dose of 50 mg per day. To the third treatment Group, Compound X is orally administered at a dose of 100 mg per day. To the fourth Group, the placebo is orally administered. All of these doses and the placebo were administered once per day. A total of 200 patients are enrolled in this treatment study.

Baseline assessments are performed at the start of treatment and these baseline results are compared with repeat assessments during various follow-up periods during the treatment study. The treatment study is conducted for twelve weeks except as indicated hereinafter. At the end of the twenty-four week period the plaque in the patients is analyzed using the Multidetector (64 slice coronary) Computerized Tomography (MDCT) scan. For patients in whom the baseline MDCT scan identifies one or more coronary noncalcified plaque index lesions of at least 1 mm in diameter in a major coronary artery, dosing of compound X or placebo is continued for a total of 6 months from initiation of therapy.

Patients receive a single daily oral dose of 25 mg, 50 mg, or 100 mg of Compound X or matching placebo by administering 2 capsules as prepared in Example 5 for 12 weeks or 24 weeks. A double-dummy design is used to achieve the proper blinding and dosages required. Thus, the groups take the following matching capsules at each daily administration of the study medication:

Placebo: two placebo capsules
25 mg dose: one placebo capsule plus one 25 mg capsule
50 mg dose: 1 placebo capsule plus one 50 mg capsule
100 mg dose: two 50 mg capsules The following baseline assessments in each of the patients are made prior to the study: history and complete physical examination; focused physical exam (for signs of bleeding disorder); 12-Lead ECG; measurement of inflammatory biomarkers (LTB4 (ex vivo) measured at trough; LTE4 urine; hsCRP; MPO; MCP1 (CCL2); M-CSF (CSF-1); MIP-2 (Cxcl2); osteopontin (Spp1)); hematology; chemistries; urinalysis; serum pregnancy test for women of childbearing potential; and 64-slice coronary MDCT imaging with contrast.

During administration of the medication in accordance with this study, the following assessments are made every 2 to 4 weeks: focused physical exam (for signs of bleeding disorders); 12-lead ECG; measurement of inflammatory biomarkers; hematology; chemistries; urinalysis; and assessments of adverse events.

After completion of administration of study medication, patients are seen one month after the last dose and the following tests completed: history and complete physical exam; focused physical exam (for signs of bleeding disorder); 12-Lead ECG; hematology; chemistries; urinalysis; serum pregnancy test for women of childbearing potential; and assessment of adverse events. Patients in whom baseline the 64-slice coronary MDCT scan identifies one or more coronary noncalcified plaque index lesions of at least 1 mm in diameter in a major coronary artery also have a 64-slice MDCT scan after completion of treatment.

The biomarker outcome measures, for determining the effectiveness of the treatment of the cardiovascular disease are defined as change from baseline after 12 weeks of dosing in the following biomarkers: LTB4, LTE4 (urine), hsCRP, MPO, MCP1, and in M-CSF, MIP-2, and osteopontin.

Based on the results, at the end of the study, a greater percentage of patients in the group treated with Compound X show a decrease in the levels of inflammatory biomarkers for cardiovascular disease over 12 weeks of dosing and a change in the density and/or plaque volume of coronary noncalcified plaque index lesions as identified by 64-slice MDCT after 24 weeks of dosing, compared to the placebo group. This demonstrates the effectiveness of Compound X in treating atherosclerotic plaque.

Example 4

This study demonstrates the efficacy of treatment with Compound X in stabilizing cardiovascular disease and atherosclerotic plaque in male and female patients with carotid stenosis undergoing elective carotid endarterectomy (CEA) surgery. In this randomized, double blind, placebo-controlled study, groups of 40 clinically stable patients between the age of 30 and 80 years with carotid stenosis undergoing elective carotid endarterectomy are treated by orally administering 100 mg of Compound X or placebo. A total of 80 patients are enrolled. Baseline assessments are performed at the start of treatment and these baseline results are compared with repeat assessments during various follow-up periods of treatment. The treatment is conducted for at least twelve weeks at which time these baseline assessments are performed and compared.

Patients receive a total single daily oral dose of 100 mg of Compound X or matching placebo by administering 2 capsules as prepared in Example 5 for 12 weeks.

The following baseline assessments in each of the patients are made: history and complete physical examination; 12-Lead ECG; carotid ultrasound; DWI-Brain MRI; measurement of ex vivo LTB4 in whole blood; spot urine for measurement of LTE4; measurement of other inflammatory biomarkers (hsCRP; MPO; MCP1 (CCL2); M-CSF (CSF-1); MIP-2 (Cxcl2); osteopontin (Spp1)); focused physical exam for signs of bleeding disorder; hematology; chemistries; urinalysis; and serum pregnancy test for women of childbearing potential.

During the period of administration of Compound X or placebo and following the last administration of compound X but prior to undergoing carotid endarterectomy, the following assessments are made every 2 to 4 weeks: 12-lead ECG; measurement of ex vivo LTB4 in whole blood; spot urine for measurement of LTE4; measurement of other inflammatory biomarkers; carotid ultrasound; focused physical exam for signs of bleeding disorder; hematology; chemistries; urinalysis; and assessment of adverse events.

Plaque samples are obtained from patients following carotid endarterectomy surgery and the samples are analyzed to determine the level of plaque tissue inflammation. The following assessments are made three days after undergoing carotid endarterectomy: DWI-MRI; chemistries; focused physical exam for signs of bleeding disorder; and assessment of adverse events. Four weeks after undergoing carotid endarterectomy, the following assessments are made: history and complete physical examination; hematology; chemistries; urinalysis; and assessment of adverse events.

The co-primary efficacy variables are: the change from baseline in ex vivo plaque LTB4 synthesis in whole blood and in ex vivo plaque LTB4 concentration after 12 weeks of administration of study medication. An analysis of covariance (ANCOVA) using the baseline level of ex vivo LTB4 synthesis in whole blood as a covariate is employed to assess significance for the first co-primary outcome. The significance of the difference between the groups with respect to the ex vivo plaque LTB4 concentrations is assessed by a t-test. Hochberg's method [Benjamani, Hochberg, Journal of the Royal Statistical Society, Series B. 57:289-300(1995)] is used to assess the significance of the co-primary outcomes. These co-primary analyses are performed on the evaluable patient population who consist of those patients who take at least one dose of study medication and who complete the 12 weeks of study according to the protocol guidelines. This analysis is repeated in the intent to treat (ITT) population which consists of all randomized patients, and the last observation carried forward (LOCF) method is employed for any missing data.

The secondary outcome measures of percent macrophage sectional area and number of T lymphocytes in plaque are analyzed using t-tests at the 0.05 alpha level (two sided). The secondary outcome measures that are changes from baseline, LTE4, hsCRP, MPO and MCP1, are analyzed using an ANCOVA with the baseline value as the covariate. The tests are done at an alpha level of 0.05 (two-sided). The evaluable patient population and ITT patient population are used in the same way as for the co-primary outcome measures.

The tertiary efficacy parameter, i.e., the number and volume of ischemic lesions assessed through brain MRI using DWI is analyzed using the nonparametric Wilcoxon rank-sum method. An alpha level of 0.05 (two sided) is assumed for significance. The evaluable patient population is used. An ITT analysis is also performed.

Based on the results, at the end of the study, a greater percentage of patients in the group treated with Compound X show a decrease in the levels of cardiovascular disease as determined by a reduction in the level of biomarkers and plaque tissue inflammation over 12 weeks of dosing and a reduction in the number of ischemic lesions [atherosclerotic plaque] after carotid endarterctomy assessed through brain MRI using DWI, compared to the placebo group.

Example 5

Capsules of Compound X were manufactured, by the following procedure.

Compound X capsules were manufactured in three strengths: 25 mg, 50 mg and 75 mg. These capsules were filled at three different fill weights of the 50% active formulation to achieve the three strengths. The ingredients and packaging components were identical for all three strengths.

Compound X capsules were manufactured using a common wet granulation made up of seven sub-batches, containing 50% Compound X, Lactose monohydrate, Pregelatinzed starch, Sodium Starch Glycolate, Povidone and USP water. The seven sub-batches were dried, milled and blended with crospovidone, glyceryl behenate, and magnesium stearate. The milled and blended material was then encapsulated to designated fill weight. The batch composition of the common granulation is shown on Table 2. The batch composition of Compound X Capsules, 25 mg is shown in Table 3, the batch composition of the Compound X Capsules, 50 mg is shown in Table 4 and the batch composition of Compound X Capsules, 75 mg is shown in Table 5

TABLE 2

Batch Composition of Compound X Capsules, Common Granulation

| Ingredient | Concentration (% w/w) | Theoretical Batch Quantity(g) |
|---|---|---|
| Common Granulation (Sub-Batches A-G) | | |
| Compound X | 50.00 | 492.9 |
| Latose, Monohydrate, NF/EP (Fastflo 316) | 24.00 | 236.6 |
| Pregelatinized Starch, NF/EP (Starch 1500) | 12.00 | 118.3 |
| Sodium Starch Glycolate, NF/EP | 5.00 | 49.3 |
| Povidone, USP/EP (D29-32) | 3.00 | 29.6 |
| Purified Water, USP/EP | —* | 410.0* |
| Purified Water, USP/EP Blending Process for Combined Sub-Batches A-G | —* | QS* |
| Crospovidone (Kollidon (CL), NF/EP | 2.00 | 138.0 |
| Glyceryl Behenate (Compritol 888 ATO), NF/EP | 3.00 | 207.0 |
| Magnesium Stearate (NonBovine HyQual R), NF/EP | 1.00 | 69.0 |
| Total | 100.0 | — |

*Water was removed by drying after wet granulation, not present in final dosage form

TABLE 3

Batch Composition of Compound X Capsules, 25 mg
Batch Size: 20,000 Capsules

| Ingredient | Concentration (% w/w) | Capsule Quantity | Batch Quantity (g) |
|---|---|---|---|
| Capsule Common Granulation | 50% | 50.0 mg | 1000.0 |
| Capsules, Hard Gelatin, Swedish Orange, Size #2 | — | 20,000 each | 20,000 capsules |

TABLE 4

Batch Composition of Compound X Capsules, 50 mg
Batch Size: 56,000 Capsules

| Ingredient | Concentration (% w/w) | Capsule Quantity | Batch Quantity (g) |
|---|---|---|---|
| Compound X Capsule Common Granulation | 50% | 100.0 mg | 5600.0 |
| Capsules, Hard Gelatin, Swedish Orange, Size #2 | — | 56,000 each | 56,000 capsules |

TABLE 5

Batch Composition of Compound X Capsules, 75 mg
Batch Size: 20,000 Capsules

| Ingredient | Concentration (% w/w) | Capsule Quantity (mg) | Batch Quantity (g) |
|---|---|---|---|
| Compound X Capsule Common Granulation | 50% | 150.0 mg | 3000 |
| Capsules, Hard Gelatin, Swedish Orange, Size #2 | | 20,000 each | 20,000 capsules |

What is claimed is:

1. A method for preventing or treating atherosclerotic plaque in human patients comprising administering to a patient a composition containing a compound of the formula:

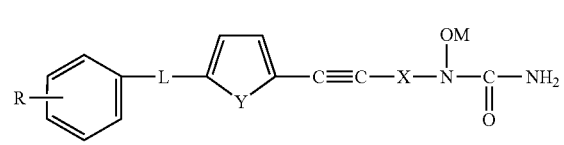

wherein R is hydrogen, lower alkyl, halogen, trifluoromethyl, lower alkoxy or hydroxy; Y is —O— or —S—; L is lower alkylene or lower alkenylene;

X is a branched- or straight-chain lower alkylene and M is selected from the group consisting of hydrogen, a pharmaceutically acceptable cation and a pharmaceutically acceptable metabolically cleavable group selected from —COR, —COOR, —CONRR and —CH$_2$OR radicals wherein R is independently selected in each occurrence from the group consisting of alkyl, trialkylsilyl, carbocyclic aryl and carbocyclic aryl substituted with one or more substituents selected from the group consisting of $C_1$-$C_4$ alkyl, halogen, hydroxy and $C_1$-$C_4$ alkoxy;

or pharmaceutically effective salts thereof with said compound being administered in an amount effective to prevent or treat atherosclerotic plaque consisting of a daily dosage of from about 0.2 to about 3.0 mg/kg of body weight.

2. The method of claim 1, wherein said administration is to treat patients who have been diagnosed as having atherosclerotic plaque.

3. The method of claim 2, wherein the treatment is to stabilize or retard the formation of further atherosclerotic plaque.

4. The method of claim 3, wherein said compound is N-[3-[5-[(4-fluorophenyl)methyl]-2-thienyl]-1-methyl-2-propynyl]-N-hydroxyurea.

5. The method of claim 3, wherein said composition is administered orally.

6. The method of claim 5, wherein said compound is N-[3-[5-[(4-fluorophenyl)methyl]-2-thienyl]-1-methyl-2-propynyl]-N-hydroxyurea.

7. The method of claim 1, wherein said administration is to patients who have had previous heart attacks or strokes caused by atherosclerotic plaque.

8. The method of claim 7, wherein the administration is for preventing or retarding the formation of atherosclerotic plaque.

9. The method of claim 8, wherein said compound is N-[3-[5-[(4-fluorophenyl)methyl]-2-thienyl]-1-methyl-2-propynyl]-N-hydroxyurea.

10. The method of claim 8, wherein said composition is administered orally.

11. The method of claim 10, wherein said compound is N-[3-[5-(4-fluorophenyl)methyl]-2-thienyl]-1-methyl-2-propynyl]-N-hydroxyurea.

12. The method of claim 1, wherein said administration is to patients which are susceptible to cardiovascular diseases.

13. The method of claim 12, wherein said administration is for retarding or preventing the formation of atherosclerotic plaque.

14. The method of claim 13, wherein said compound is N-[3-[5-[(4-fluorophenyl)methyl]-2-thienyl]-1-methyl-2-propynyl]-N-hydroxyurea.

15. The method of claim 13, wherein said composition is administered orally.

16. The method of claim 15, wherein said compound is N-[3-[5-[(4-fluorophenyl)methyl]-2-thienyl]-1-methyl-2-propynyl]-N-hydroxyurea.

17. A composition in unit dosage form for oral administration comprising as an active ingredient a compound of the formula:

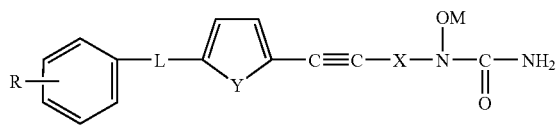

wherein R is hydrogen, lower alkyl, halogen, trifluoromethyl, lower alkoxy or hydroxy; Y is —O— or —S—; L is lower alkylene or lower alkenylene; X is a branched— or straight—chain lower alkylene and M is selected from the group consisting of hydrogen, a pharmaceutically acceptable cation and a pharmaceutically acceptable metabolically cleavable group selected from —COR, —COOR, —CONRR and —CH$_2$OR radicals wherein R is indenendently selected in each occurrence from the group consisting of alkyl, trialkylsilyl, carbocyclic aryl and carbycyclic aryl substituted with one or more substituents selected from the group consisting of $C_1$-$C_4$ alkyl, halogen, hvdroxy and $C_1$-$C_4$ alkoxy;

or a pharmaceutically accepted salt thereof, said active ingredient being present in an amount selected from the group consisting of 25 mg, 50 mg and 75 mg.

18. The composition of claim 17, wherein said active ingredient is N-[5-[5-[(4-fluorophenyl)methyl]-2-thienyl]-1-methyl-2-propynyl]-N-hydroxyurea.

19. The composition of claim 18, wherein said unit oral dosage form is a tablet or capsule.

20. The composition of claim 19, wherein said active ingredient is N-[3-[5-[(4-fluorophenyl)methyl]-2-thienyl]-1-methyl-2-propynyl]-N-hydroxyurea.

\* \* \* \* \*